(12) United States Patent
Miller et al.

(10) Patent No.: US 7,480,973 B2
(45) Date of Patent: Jan. 27, 2009

(54) AUTOMATED MARKER BAND NEST PLACEMENT CRIMPER

(75) Inventors: Joseph Miller, Coon Rapids, MN (US); Chrismar Scribner, Edina, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 232 days.

(21) Appl. No.: 10/790,941

(22) Filed: Mar. 1, 2004

(65) Prior Publication Data

US 2005/0192498 A1 Sep. 1, 2005

(51) Int. Cl.
*B25B 27/14* (2006.01)

(52) U.S. Cl. ............................ 29/272; 29/517; 29/559; 29/281.1

(58) Field of Classification Search .................. 29/464, 29/466, 468, 559, 281.1, 516, 517, 518, 272
See application file for complete search history.

(56) References Cited

U.S. PATENT DOCUMENTS

| | | | | |
|---|---|---|---|---|
| 407,037 | A | * 7/1889 | Robertson | 29/517 |
| 2,314,236 | A | * 3/1943 | Mott | 285/256 |
| 2,639,754 | A | * 5/1953 | Macy | 72/411 |
| 2,692,422 | A | * 10/1954 | Pierce | 29/865 |
| 2,802,257 | A | * 8/1957 | Holtzapple | 29/862 |
| 3,055,412 | A | * 9/1962 | Dibner | 72/470 |
| 3,085,313 | A | * 4/1963 | Macy | 29/862 |
| 4,733,665 | A | 3/1988 | Palmaz | 128/343 |
| 4,740,207 | A | 4/1988 | Kreamer | 623/1 |
| 4,944,071 | A | 7/1990 | Marzoli et al. | 19/80 R |
| 5,007,926 | A | 4/1991 | Derbyshire | 623/1 |
| 5,070,608 | A | * 12/1991 | Gray | 29/890.044 |
| 5,138,864 | A | 8/1992 | Tarpill | 72/410 |
| 5,692,294 | A | 12/1997 | Casey | 29/753 |
| 5,723,004 | A | 3/1998 | Dereume et al. | 623/1 |

(Continued)

FOREIGN PATENT DOCUMENTS

EP 0 916 318 5/1999

(Continued)

OTHER PUBLICATIONS

Palmaz et al., "Expandable Intraluminal Graft: A Preliminary Study", *Radiology*, vol. 156, No. 1, pp. 73-77 (Jul. 1985).

*Primary Examiner*—Jermie E Cozart
(74) *Attorney, Agent, or Firm*—Crompton, Seager & Tufte, LLC

(57) ABSTRACT

A positioning assembly for automatically positioning a first cylindrical member for crimping to a second cylindrical member has a first plate and a second plate. The first plate has a nest to accommodate at least a portion of the first cylindrical member and/or at least a portion of the second cylindrical member. The second plate has a nest to accommodate at least a portion of the first cylindrical member and/or at least a portion of the second cylindrical member. The first plate is constructed and arranged to be separated from the second plate in a first position. In a second position the first plate is immediately adjacent to the second plate. When in the second position, the first plate and the second plate are situated such that the first cylindrical member and the second cylindrical member would be in proper placement for joining.

17 Claims, 3 Drawing Sheets

U.S. PATENT DOCUMENTS

| | | | |
|---|---|---|---|
| 5,725,519 A | 3/1998 | Penner et al. | 606/1 |
| 5,755,735 A | 5/1998 | Richter et al. | 606/194 |
| 5,810,873 A | 9/1998 | Morales | 606/198 |
| 5,836,952 A | 11/1998 | Davis et al. | 606/108 |
| 5,893,852 A | 4/1999 | Morales | 606/108 |
| 5,920,975 A | 7/1999 | Morales | 29/282 |
| 5,974,652 A | 11/1999 | Kimes et al. | 29/516 |
| 5,992,000 A | 11/1999 | Humphrey et al. | 29/516 |
| 6,063,102 A | 5/2000 | Morales | 606/198 |
| 6,082,990 A | 7/2000 | Jackson et al. | 425/517 |
| 6,108,886 A | 8/2000 | Kimes et al. | 29/280 |
| 6,125,523 A | 10/2000 | Brown et al. | 29/516 |
| 6,141,855 A | 11/2000 | Morales | 29/516 |
| 6,149,680 A | 11/2000 | Shelso et al. | 623/1.11 |
| 6,167,605 B1 | 1/2001 | Morales | 29/282 |
| 6,277,110 B1 | 8/2001 | Morales | 606/1 |
| 6,352,547 B1 | 3/2002 | Brown et al. | 606/198 |
| 6,360,577 B2 | 3/2002 | Austin | 72/402 |
| 6,364,870 B1 * | 4/2002 | Pinchasik | 606/1 |
| 6,387,117 B1 * | 5/2002 | Arnold et al. | 623/1.1 |
| 6,481,262 B2 * | 11/2002 | Ching et al. | 72/416 |
| 6,510,722 B1 | 1/2003 | Ching et al. | 72/402 |
| 6,568,235 B1 | 5/2003 | Kokish | 72/402 |
| 6,569,192 B1 | 5/2003 | Foreman et al. | 623/1.11 |
| 6,629,350 B2 | 10/2003 | Motsenbocker | 29/283.5 |
| 6,640,412 B2 | 11/2003 | Iancea | 29/505 |
| 6,651,478 B1 | 11/2003 | Kokish | 72/402 |
| 2002/0138966 A1 | 10/2002 | Motenbocker | 29/516 |
| 2002/0161426 A1 | 10/2002 | Iancea | 623/1.11 |
| 2003/0056360 A1 | 3/2003 | Brown et al. | 29/516 |
| 2003/0150250 A1 | 8/2003 | Shortt | 72/235 |
| 2003/0192164 A1 | 10/2003 | Austin | 29/505 |

FOREIGN PATENT DOCUMENTS

| | | |
|---|---|---|
| FR | 2 797 391 | 2/2001 |
| WO | WO 98/19633 | 5/1998 |

* cited by examiner

AUTOMATED MARKER BAND NEST PLACEMENT CRIMPER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Medical devices such as stents, stent-grafts, grafts, or vena cava filters and catheters, balloon catheters, and medical balloons for their delivery are utilized in a number of medical procedures and situations, and as such their structure and function are well known.

Catheters for example, may be used in a variety of medical procedures. An example of one potential use for a catheter is in PTCA procedures. In typical PTCA procedures, a guiding catheter is percutaneously introduced into the cardiovascular system of a patient through a vessel and advanced through therein until the distal end thereof is at a desired location in the vasculature. A guidewire and a dilatation catheter having a balloon on the distal end thereof are introduced through the guiding catheter with the guidewire sliding through the dilatation catheter. The guidewire is first advanced out of the guiding catheter into the patient's coronary vasculature and the dilatation catheter is advanced over the previously advanced guidewire until the dilatation balloon is properly positioned across the lesion. Once in position across the lesion, the flexible, expandable, preformed balloon is inflated to a predetermined size with a liquid at relatively high pressures, to radially compress the arthrosclerotic plaque of the lesion against the inside of the artery wall and thereby dilate the lumen of the artery. The balloon is then deflated to a small profile so that the dilatation catheter may be withdrawn from the patient's vasculature and blood flow resumed through the dilated artery.

In angioplasty procedures of the kind described above, there may be injury to or restenosis of the artery, which either necessitates another angioplasty procedure, a surgical bypass operation, or some method of repairing or strengthening the area. To strengthen the area and help prevent restenosis, a physician can implant an intravascular prosthesis for maintaining vascular patency, commonly called a stent, inside the artery at the lesion. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. No. 4,740,207 to Kreamer and U.S. Pat. No. 5,007,926 to Derbyshire, the content of which is incorporated herein by reference. Palmaz et al., 156 *Radiology* 73 (1985) and U.S. Pat. No. 4,733,665 describe introduction of a stent over a balloon catheter (incorporated herein by reference).

To assist in accurate placement of the catheter and stent underneath the lesion site it is useful to visually monitor the catheter as it advances through a vessel. Fluoroscopes or other similar X-ray emitting devices are used to view the catheter within the body as it is advanced. However, in order for the catheter to be visible when exposed to X-rays, the catheter or a portion of the catheter, must be radiopaque to X-rays. In previous catheter designs, radiopaque marker bands, stent retaining members, hubs, catheter tips, or other components have been attached to the catheter for this purpose.

In addition to utilizing radiopaque marker bands for observing the catheter as it is advanced through a body lumen, radiopaque materials may also be utilized in the formation of other potential catheter components such as hubs, bumpers, stops and others.

Marker bands are often crimped onto the inner tube of the catheter. It is important to have accurate placement when aligning the marker bands about the inner tube prior to crimping. This alignment process has previously been done by hand. However, depending on the experience of the operator, this process can be more time consuming and less precise than desired. In light of the above, it would be desirable to provide an automated component to the crimping mechanism which facilitates accurate placement of the marker bands at a more desirable rate of speed.

There yet remains a need for an automated component to the crimping mechanism which facilitates accurate placement of the marker bands at a more desirable rate of speed.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a positioning assembly of a crimper apparatus may automatically position a first cylindrical member for crimping to a second cylindrical member. In at least another embodiment a first plate may have a nest to accommodate at least a portion of the first cylindrical member and/or at least a portion of the second cylindrical member, and a second plate may have a nest to accommodate at least a portion of the first cylindrical member and/or at least a portion of the second cylindrical member. In at least one embodiment the first plate may be constructed and arranged to be separated from the second plate in a first position, and in a second position the first plate may be immediately adjacent to the second plate. In the second position the first cylindrical member and the second cylindrical member may be in proper placement for joining.

In at least one embodiment, at least one plate may have a nest longitudinally aligned with a nest on the second plate.

In at least one embodiment, at least one plate may have a nest longitudinally aligned with a nest on the second plate and with a nest on a third plate; the third plate may be immediately adjacent to the second plate.

In at least one embodiment, the positioning assembly may have a first biasing member which may maintain the first position when activated.

In at least one embodiment, the positioning assembly may have a second biasing member which may maintain the second position when the first biasing member is not activated.

In at least one embodiment, the positioning assembly may have as a first biasing member at least one solenoid.

In at least one embodiment, the positioning assembly may have a second biasing member comprising a spring loaded force.

In at least one embodiment, the plates may be spring loaded such that when the solenoids are not activated the second position may be maintained.

In at least one embodiment, both the first and the second plate may have a plurality of nests. At least two nests on the first plate may be longitudinally unaligned from one another and longitudinally aligned with nests on the second plate.

In at least one embodiment, a third plate may have at least two nests which are longitudinally unaligned with one another and longitudinally aligned with nests on the first plate and the second plate.

In at least one embodiment, the first cylindrical member may be a radiopaque marker band, a stent retaining member, a hub, a catheter tip, or any combination thereof.

In at least one embodiment, the second cylindrical member may be a catheter tube.

In at least one embodiment, the second cylindrical member may be the inner tube of a catheter.

In at least one embodiment, the first cylindrical member is crimped to the second cylindrical member by disposing the first cylindrical member about the second cylindrical member, disposing the first cylindrical member and the second cylindrical member into the nests of the apparatus, activating the apparatus such that the plates move from the first position to the second position, crimping the first cylindrical member to the second cylindrical member.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a preferred embodiment to the invention.

BRIEF DESCRIPTION OF THE SEVERAL VIEWS OF THE DRAWINGS

Referring to the Drawings, wherein like numerals represent like parts throughout the several views.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
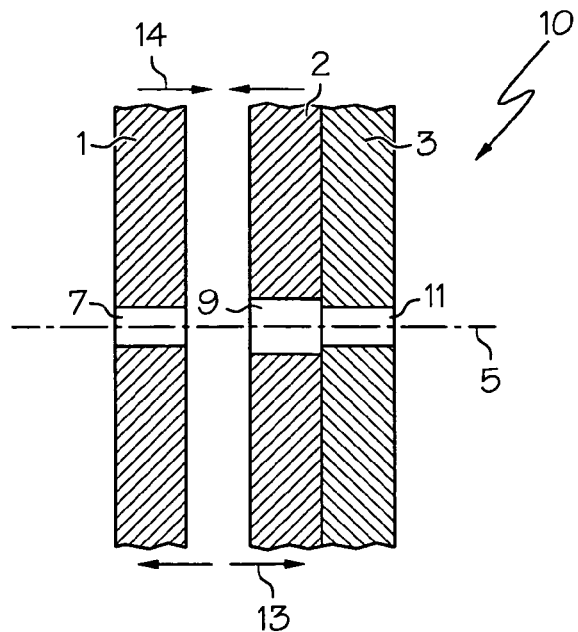
FIG. 1 is a plan view of the apparatus with a plate separate from the other plates.

Referring now to FIG. 1, in at least one embodiment of the invention a positioning assembly 10 comprises a first plate 1, a second plate 2, and a third plate 3 having nests 7, 9, and 11 respectively. Each nest is a recess in the respective plate. Nests may be longitudinally aligned about a longitudinal axis 5. The nests may be sized to fittingly receive various items such as a catheter shaft and marker band, or other tubular devices to be seated therein and subsequently positioned and joined together in a desired configuration in the manner discussed below. The nests may vary in diameter depending in part on the dimensions and configuration of the items to be joined together. In the various figures shown and described herein, nests 7 and 11 have similar diameters so as to be sized to nest a tube or other elongate member. Nest 9 in FIG. 1 is sized to nest the larger diameter item, such as a marker band or other tubular member, about the smaller diameter elongate member, such as the shaft of a catheter, etc. It should be noted that in some applications more plates may be used and each plate may include a single nest or multiple nests. These nests may comprise elaborate and/or complex geometries in addition to or other than the substantially concave recesses shown in FIG. 1. It should also be noted that each of the plates shown in the figures may also consist of multiple plates constructed and arranged to have a geometry substantially identical to an individual plate.

Figure 2:
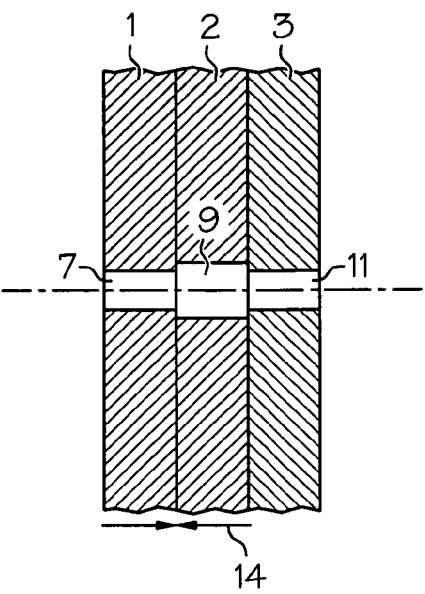
FIG. 2 is a plan view of the apparatus with the plates contacting one another.

In at least one embodiment of the invention, FIG. 1 illustrates that the first plate 1 may be separated from the other plates through the use of a first biasing force 13. A first biasing force may be provided by any biasing mechanism such as for example by the use of activated solenoids, air cylinders, etc. When the plates are separated, by such biasing force, the plates are in the first position. When the first biasing force 13 separating the plates is not activated the biasing force may be greatly diminished or negligible such that the plates may come together under a second biasing force 14. The second biasing force may be present in the first position but weaker than that of the first biasing force, or the first biasing force may be present in the second position but weaker than that of the second biasing force. In at least one embodiment the second biasing force is not activated when in the first position. In at least another embodiment the first biasing force may not be activated when in the second position. In at least one embodiment of the invention the first biasing force may overcome the second biasing force in order to maintain the first position. This second biasing force may be generated through air pressurizing or spring loading the at least one plate. Springs, air cylinders, solenoids, and/or magnets may be used as the second biasing force. In this position the plates may be substantially in contact as shown in FIG. 2.

Figure 2A:
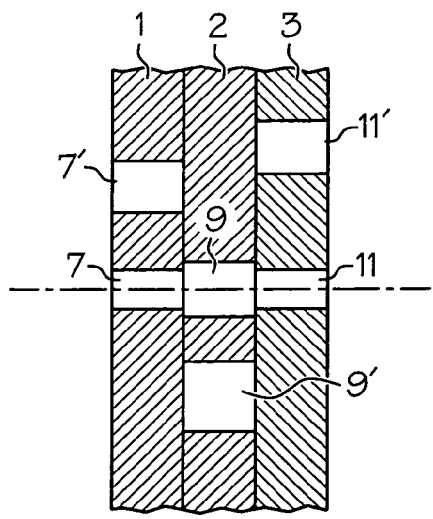
FIG. 2a is a plan view of the apparatus illustrating plates having multiple nests.
Figure 3:
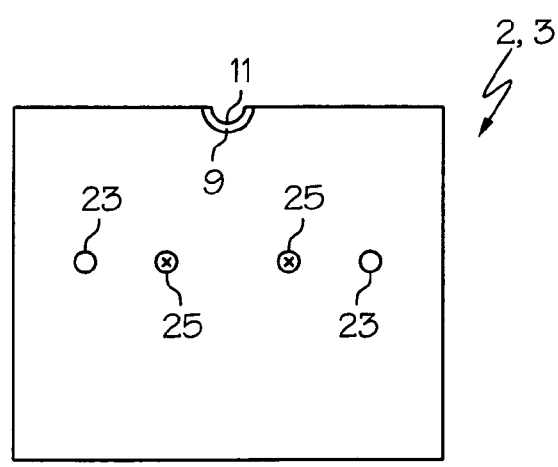
FIG. 3 is a side view of the plates illustrating the nests of the plates.

FIG. 3 illustrates a side view of the plates 2, 3 including dowel holes 23 and affixing holes 25. The second plate 2 may be affixed to the third plate 3 through affixing holes 25. Screws may be used to affix the plates together. The first plate 1 (not shown), the second plate 2 and the third plate 3 may slide along a dowel or rod that may be disposed within the dowel holes 23. Frictional forces must be overcome when moving the first plate 1 into contact with the second plate 2 or when moving the plates out of contact with one another. In order to better accommodate the potentially greater diameter of a marker band in relation to the catheter shaft plate 2 may have a nest 9 more deeply recessed than the nest 11 of plate 3. The less deeply recessed nest 11 of third plate 3 provides an edge inhibiting movement of a marker band disposed in the more deeply recessed nest 9 upon movement of the first plate 1 when the second position is being reached. It should also be noted that a single plate may be constructed having dimensions and nests substantially identical to the combination of plates 2 and 3. As shown in FIG. 2a, it should also be noted that each plate may have multiple nests (7 and 7', 9 and 9', and 11 and 11') with recessed portions of a wide range of geometries. In addition, the plates may be adjustable so they may slide in a direction normal to the longitudinal 5. Thus, by sliding one plate, various recessed portions in one plate may be longitudinally aligned to a single recessed portion of another plate. This may aid in adjusting the assembly for first cylindrical members and/or second cylindrical members of different sizes.

Figure 4:
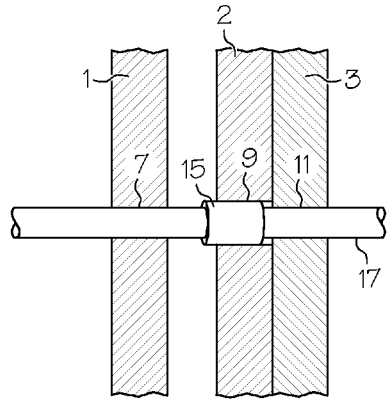
FIG. 4 is a plan view of the apparatus with a plate separate from the other plates and with a catheter and marker band in the nests.

In FIG. 4 the nests 7,9,11 have disposed upon them a tubular or partially tubular member 15 such as a marker band disposed about an elongate body 17 such as a portion of a catheter shaft. The tubular member 15 may be a radiopaque marker band, a stent retaining member such as a hub, a separate catheter tip, or any other device of which engagement to a catheter shaft is desired.

Figure 5:
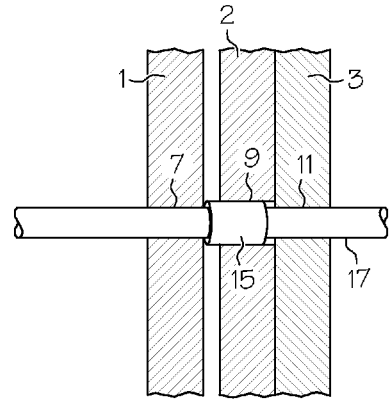
FIG. 5 is a plan view of the apparatus with a plate separate from the other plates and with a catheter and marker band in the nests and the plate closer in proximity to the other plates.
Figure 6:
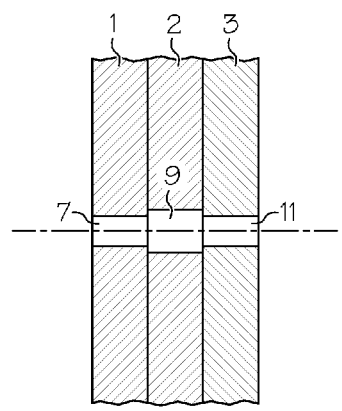
FIG. 6 is a plan view of the apparatus with the plates in contact with one another and with a catheter and marker band in the nests.
Figure 7:
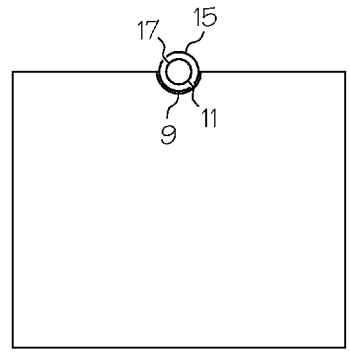
FIG. 7 is a side view of the plates illustrating the nests of the plates as well as a cross-sectional view of the catheter and marker band.

In order to properly position the tubular member 15 onto the shaft 17, the tubular member may be disposed about the shaft 17 in any manner desired and the exposed ends of the elongate body 17 may be fittingly disposed in nests 7,11, while the tubular member 15 is partially fittingly disposed in nest 9. As shown in FIG. 5 the first biasing force may be deactivated and the first plate 1 acquiesces to the second biasing force such that the first plate 1 may contact the tubular member 15 as it moves toward the other plates. The tubular member 15 has a diameter greater than that of the nest 7 of plate 1, thus tubular member 15 may be moved over as the first plate 1 moves toward and against the adjacent plate 2. In FIG. 6 the plates are in the second position wherein the tubular member 15 and the elongate body 17 are aligned in the desired positioned. FIG. 7 illustrates the side view of plates 2, 3 wherein the tubular member 15 is disposed in nest 9 and the elongate body 17 is disposed in nest 11. After the tubular member 15 and elongate member 17 are joined they may be removed from the nests 7,9,11. With the first biasing force again activated, the first position may be maintained as shown in FIG. 1. Where the tubular member 15 is a marker band and the elongate body 17 is a catheter shaft, once positioned in the manner described, the marker band 15 may be crimped or otherwise fixedly engaged to the catheter shaft 17 to prevent undesired longitudinal displacement.

Figure 8:
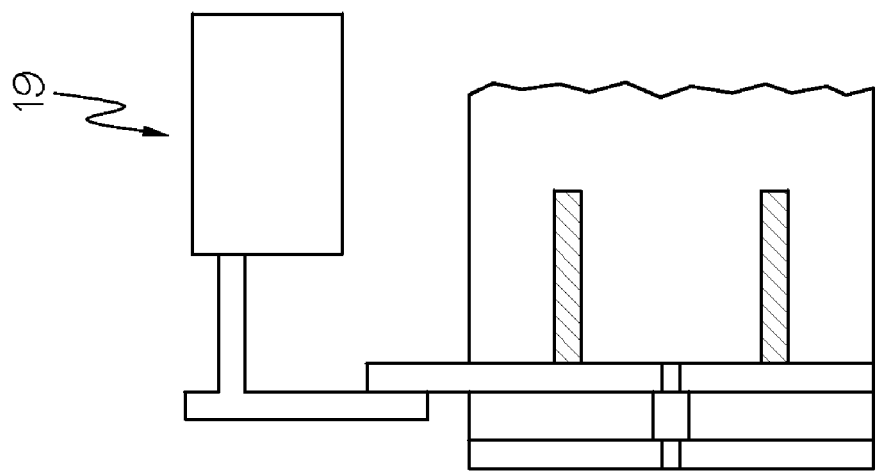
FIG. 8 is a top view of a positioning assembly with two sets of plates and illustrating hardware in block diagram of the first biasing force and the second biasing force.
Figure 8:
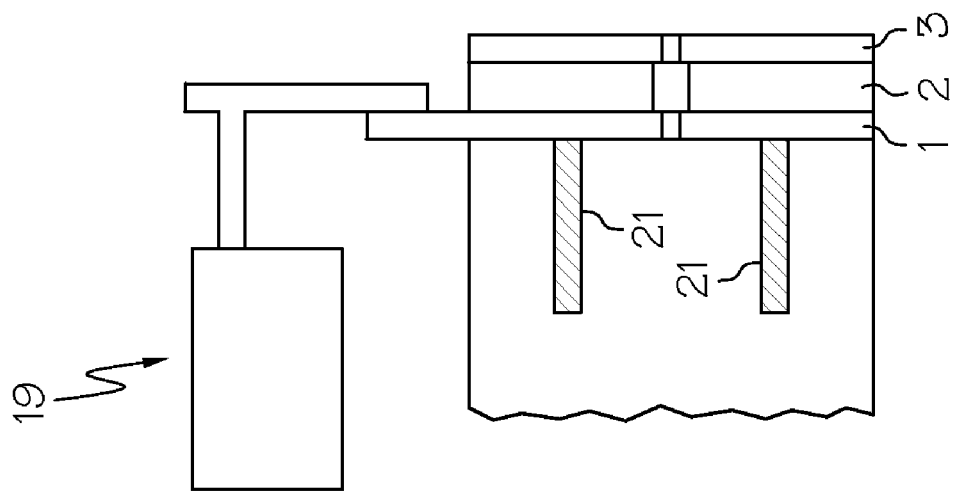

In FIG. 8 two plate sets of the positioning assembly include the biasing members which generate the first and second biasing forces. First biasing member 19 may exert a first biasing force on the first plate 1 such that the first plate 1 may be separated from the second plate 2 and the third plate 3 such that the positioning assembly 10 is in the open position as shown in FIG. 1. The second biasing force exerted by second biasing member 21 is overcome by the first biasing force exerted by first biasing member 19 when in the first position. First biasing member 19 may be a solenoid which, when activated, may exert a biasing force greater than the biasing force of second biasing member 21 which may be a spring which may provide a substantially constant force. When the first biasing member is not activated, the second biasing member may close the plates into the second position. In order to return to the closed position, the second biasing member 21 must overcome the frictional forces that may exist between the plates and the dowel or rod which may reside in dowel holes 23.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A positioning assembly of a crimper apparatus for automatically positioning a second cylindrical member for crimping to a first cylindrical member, the first cylindrical member defining a longitudinal axis, the positioning device comprising:
    a first plate and a second plate, the first plate having a first nest to accommodate at least a portion of the first cylindrical member, the second plate having a second nest to accommodate at least a portion of the second cylindrical member, the first nest and the second nest aligned along the longitudinal axis,
    the first plate moveable relative to the second plate along the longitudinal axis, in a first position the first plate separated from the second plate along the longitudinal axis, and in a second position the first plate closer to the second plate than in the first position, when in the second position the first plate and the second plate situated such that the first cylindrical member and the second cylindrical member would be in predetermined placement for joining;
    wherein the first plate contacts the second plate when in the second position.

2. The positioning assembly of claim 1, wherein the first nest is coaxially aligned with the second nest.

3. The positioning assembly of claim 2, further comprising a third nest that is coaxially aligned with the first nest.

4. The positioning assembly of claim 1, wherein the first cylindrical member is selected from the group consisting of radiopaque marker bands, stent retaining members, hubs, catheter tips, or any combination thereof.

5. The positioning assembly of claim 4, wherein the second cylindrical member is a catheter tube.

6. The positioning assembly of claim 4, wherein the second cylindrical member is the inner tube of a catheter.

7. A positioning assembly of a crimper apparatus for automatically positioning a first cylindrical member for crimping to a second cylindrical member comprising:
    a first plate and a second plate, the first plate having a nest to accommodate at least a portion of the first cylindrical member, the second plate having a nest to accommodate at least a portion of the first cylindrical member and/or at least a portion of the second cylindrical member, both the first cylindrical member and the second cylindrical member having a longitudinal axis extending in a longitudinal direction;
    the first plate moveable relative to the second plate in the longitudinal direction, in a first position the first plate separated from the second plate in the longitudinal direction, and in a second position the first plate immediately adjacent to the second plate, when in the second position the first plate and the second plate situated such that the first cylindrical member and the second cylindrical member would be in predetermined placement for joining;

wherein the first plate has a nest longitudinally aligned with a nest on the second plate and with a nest on a third plate, the third plate immediately adjacent to the second plate.

8. A positioning assembly of a crimper apparatus for automatically positioning a second cylindrical member for crimping to a first cylindrical member, the first cylindrical member defining a longitudinal axis, the positioning device comprising:

a first plate and a second plate, the first plate having a first nest to accommodate at least a portion of the first cylindrical member, the second plate having a second nest to accommodate at least a portion of the second cylindrical member, the first nest and the second nest aligned along the longitudinal axis, the first plate moveable relative to the second plate along the longitudinal axis, in a first position the first plate separated from the second plate along the longitudinal axis, and in a second position the first plate closer to the second plate than in the first position, when in the second position the first plate and the second plate situated such that the first cylindrical member and the second cylindrical member would be in predetermined placement for joining;

wherein a first biasing member biases the first plate toward the first position when activated.

9. The positioning assembly of claim 8, wherein a second biasing member biases the first plate toward the second position when the first biasing member is not activated.

10. The positioning assembly of claim 9 wherein the second biasing member comprises a spring.

11. The positioning assembly of claim 8 wherein the first biasing member is at least one solenoid.

12. A positioning assembly of a crimper apparatus for automatically positioning a second cylindrical member for crimping to a first cylindrical member, the first cylindrical member defining a longitudinal axis, the positioning device comprising:

a first plate and a second plate, the first plate having a first nest to accommodate at least a portion of the first cylindrical member, the second plate having a second nest to accommodate at least a portion of the second cylindrical member, the first nest and the second nest aligned along the longitudinal axis, the first plate moveable relative to the second plate along the longitudinal axis, in a first position the first plate separated from the second plate along the longitudinal axis, and in a second position the first plate closer to the second plate than in the first position, when in the second position the first plate and the second plate situated such that the first cylindrical member and the second cylindrical member would be in predetermined placement for joining;

the second plate further comprising a third nest, the third nest offset from the second nest in a direction lateral to the longitudinal axis.

13. The positioning assembly of claim 12, wherein the second plate is moveable to align the third nest with the first nest along the longitudinal axis.

14. The positioning assembly of claim 12, wherein the second nest and the third nest have different geometries.

15. The positioning assembly of claim 12, the first plate further comprising a fourth nest, the fourth nest offset from the first nest in a direction lateral to the longitudinal axis.

16. The positioning assembly of claim 15, wherein the first plate is moveable to align the fourth nest with the second nest along the longitudinal axis.

17. A positioning assembly of a crimper apparatus for automatically positioning a marker for crimping to a catheter comprising:

a first plate and a second plate, the first plate having a first nest to accommodate at least a portion of the catheter, the second plate having a second nest to accommodate at least a portion of the marker, the first plate and the second plate moveable relative to one another to adjust a distance between the first nest and the second nest as measured along the length of the catheter;

the positioning assembly further comprising a third nest, the third nest and the first nest located on opposite sides of the second nest, the third nest accommodating at least a portion of the catheter.

* * * * *